United States Patent
Nakamura et al.

(10) Patent No.: US 6,365,782 B1
(45) Date of Patent: Apr. 2, 2002

(54) PRODUCTION OF TRICYCLODECANE DICARBALDEHYDE, PENTACYCLOPENTADECANE DICARBALDEHYDE AND CORRESPONDING DIMETHANOLS

(75) Inventors: Kenichi Nakamura; Kazuhiro Yamada; Takashi Fujii; Takashi Motoi, all of Ibaraki-ken (JP)

(73) Assignee: Mitsbushi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 09/609,374

(22) Filed: Jul. 3, 2000

(30) Foreign Application Priority Data

Jul. 2, 1999 (JP) .......... 11-188687
Jul. 2, 1999 (JP) .......... 11-188688
Dec. 13, 1999 (JP) .......... 11-353551

(51) Int. Cl.$^7$ .......... C07C 45/50; C07C 29/16
(52) U.S. Cl. .......... 568/444; 568/445; 568/817; 568/822; 568/838; 568/909
(58) Field of Search .......... 568/444, 445, 568/817, 822, 838, 909

(56) References Cited

U.S. PATENT DOCUMENTS

| 2,880,241 A | 3/1959 | Hughes |
| 3,499,932 A | 3/1970 | Pruett et al. |
| 3,499,933 A | 3/1970 | Pruett et al. |
| 4,144,191 A | 3/1979 | Hartwell et al. |
| 4,262,147 A | 4/1981 | Garrou et al. |
| 4,292,196 A | * 9/1981 | Homeier et al. ........ 252/412 |
| 5,138,101 A | 8/1992 | Devon |
| 5,260,490 A | 11/1993 | Förster et al. |
| 5,773,667 A | 6/1998 | Bahrmann et al. |
| 5,817,884 A | 10/1998 | Bahrmann |

FOREIGN PATENT DOCUMENTS

| EP | 0186075 | 7/1986 |
| EP | 0374615 | 6/1990 |
| GB | 750144 | 6/1956 |
| GB | 1170226 | 11/1969 |
| JP | 55-118429 | 9/1980 |
| JP | 63-119429 | 5/1988 |
| JP | 11-80067 | 3/1999 |
| JP | 11-80068 | 3/1999 |
| JP | 11-100339 | 4/1999 |
| WO | WO93/02024 | 2/1993 |

OTHER PUBLICATIONS

Database WPI, Derwent Publications, Ltd., Abstract for JP56030938, Mar. 28, 1981 (Week 198120).

Database WPI, Derwent Publications, Ltd., Abstract for JP53068709, Jun. 19, 1978 (Week 197830).

* cited by examiner

Primary Examiner—Sreeni Padmanabhan
(74) Attorney, Agent, or Firm—Antonelli, Terry, Stout & Kraus, LLP

(57) ABSTRACT

A method of producing tricyclodecane dicarbaldehyde and/or pentacyclopentadecane dicarbaldehyde by the hydroformylation of dicyclopentadiene and/or tricyclopentadiene. The tricyclodecane dicarbaldehyde and/or pentacyclopentadecane dicarbaldehyde in the hydroformylation product liquid are extracted with an extraction solvent comprising a polyhydric alcohol having 2 to 6 carbon atoms. With such extraction, the tricyclodecane dicarbaldehyde and/or pentacyclopentadecane dicarbaldehyde transfer into the extraction solvent while retaining the catalyst components in the hydroformylation solvent. The controlled extraction atmosphere with an oxygen concentration of 1000 ppm or lower prevents the rhodium compound from transferring into the extraction solvent, thereby avoiding the loss of expensive rhodium. The extraction solvent containing tricyclodecane dicarbaldehyde and/or pentacyclopentadecane dicarbaldehyde as such can be directly subjected to catalytic hydrogenation to produce corresponding tricyclodecane dimethanol and/or pentacyclopentadecane dimethanol.

18 Claims, No Drawings

PRODUCTION OF TRICYCLODECANE DICARBALDEHYDE, PENTACYCLOPENTADECANE DICARBALDEHYDE AND CORRESPONDING DIMETHANOLS

BACKGROUND OF THE INVENTION

1. Field of the Invention

The present invention relates to a method of producing dialdehydes (tricyclodecane dicarbaldehyde and/or pentacyclopentadecane dicarbaldehyde) by hydroformylation of dicyclopentadiene and/or tricyclopentadiene, and a method of producing dimethanols (tricyclodecane dimethanol and pentacyclopentadecane dimethanol) by hydrogenating the dialdehydes.

Tricyclodecane dimethanol and pentacyclopentadecane dimethanol which are produced by reducing tricyclodecane dicarbaldehyde and pentacyclopentadecane dicarbaldehyde with hydrogen are useful as materials for producing polyesters, polyester carbonates, acrylic resins, methacrylic resins, etc. Particularly, polycarbonate resins having constitutional units derived from tricyclodecane dimethanol and/or pentacyclopentadecane dimethanol have excellent properties as optical materials for manufacturing optical disks, optical fibers, spectacle lenses, lenses for industrial use, etc. With such usefulness, it has been demanded to develop industrial method of easily producing the dialdehydes. In addition, tricyclodecane dimethanamine and pentacyclopentadecane dimethanamine which are produced by reductive amination of tricyclodecane dicarbaldehyde and pentacyclopentadecane dicarbaldehyde are useful as materials for producing polyamide resins and isocyanates.

The present invention further relates to a method of recovering high-boiling dialdehydes produced by rhodium/organophosphorus-catalyzed hydroformylation of dicyclopentadiene and/or tricyclopentadiene in a hydroformylation solvent comprising a hydrocarbon compound. More particularly, the present invention relates to a method of recovering a high-boiling dialdehyde from a reaction product liquid containing a rhodium-organophosphorus catalyst, a dialdehyde and a hydroformylation solvent obtained from liquid reaction product-take-off, hydroformylation process. The hydroformylation is well-known in the art as a method of converting olefins into aldehydes having one carbon more than the starting olefins by the addition of one molecule each of hydrogen and carbon monoxide to one carbon-carbon double bond. If the organic substrate contains two or more carbon-carbon double bonds, two or more formyl groups can be added to the substrate, thereby increasing the number of carbon atoms in the substrate by two or more. As a result, both the molecular weight and the boiling point of the aldehyde produced increase significantly when the starting olefin has a substituent group such as carboxyl, aldehyde and hydroxyl as well as when the starting olefin constituted only by hydrogen and carbon has six or more carbon atoms. Therefore, there are demands for establishing industrial process for easily recovering the high-boiling aldehydes.

2. Description of the Prior Art

The production of tricyclodecane dicarbaldehyde by hydroformylation of dicyclopentadiene is known. British Patent No. 750144 discloses to hydroformylate dicyclopentadiene in the presence of a diluent, a polymerization inhibitor, a stabilizer and a catalyst comprising a cobalt compound.

EP-A-186075 teaches to hydroformylate dicyclopentadiene in the presence of a catalyst comprising a rhodium compound and a quaternary ammonium salt of phosphine having a sulfonic acid group.

WO93/02024 describes the extraction of high-boiling aldehydes produced by rhodium-catalyzed hydroformylation of olefins with an extraction solvent comprising a primary alkanol and water.

U.S. Pat. No. 5,260,490 describes to separate and recover rhodium catalysts with an aqueous solution of complex-forming organic phosphine, thereby recycling and reusing the recovered rhodium catalysts.

Japanese Patent Application Laid-Open Nos. 11-80067 and 11-80068 teach hydroformylation of dicyclopentadiene in the presence of a rhodium catalyst of extremely reduced concentration using a phosphite ligand while controlling a conjugated diene concentration.

The production of aldehydes by hydroformylation has been industrially practiced using a rhodium-organophosphorus compound catalyst on lower olefins such as ethylene and propylene. In this production, the aldehyde produced are separated from the catalyst components by distillation. Since the rhodium-organophosphorus compound catalyst is poor in heat stability, the low-boiling aldehydes produced in the above process are recovered as vapor from the mixture containing high-boiling products by gas stripping using unreacted gas. This method is successful for aldehydes having relatively low boiling points due to their relatively high vapor pressure at hydroformylation temperatures employed. However, the flow rate of stripping gas should be increased with increasing boiling point of aldehyde to obtain the aldehyde in the same yield, this making the process less practical. In another method of recovering the products, the high-boiling products are separated from the catalyst by distilling the high-boiling residue containing the catalyst under reduced pressure at high temperatures. However, the problem of this method is a loss of expensive rhodium metal from hydroformylation process by its deposition onto the surface of apparatus due to poor heat stability of the catalyst.

As alternative method to the distillation for recovering the high-boiling aldehyde, proposed are extraction separation, membrane separation and immobilization of catalyst (general reviews in J. of Mol. Cat. A., 104(1995), pp 17–85; J. of Mol. Cat. A., 116(1997), pp39–42; and J. of Cat. Soc. of Japan, vol. 39, No. 5(1997), pp341–346).

As a process utilizing extraction separation, put into practice is a hydroformylation of propylene in a two-phase organic solvent/water system using a rhodium catalyst containing water-soluble trisulfonated-triphenylphosphine sodium salt as ligands. The water layer containing the catalyst from phase separation after the reaction is reused in the next run. This hydroformylation process in organic solvent/water two-phase system is taught to be applicable to the hydroformylation of butene isomer mixtures. However, olefins become less soluble to water with increasing number of carbon atoms, and therefore, the process is not practical for higher olefins due to low reaction rate.

WO93/02024, as mentioned above, describes the extraction of high-boiling aldehydes produced by rhodium-catalyzed hydroformylation of olefins with an extraction solvent comprising a primary alkanol and water.

The membrane separation for separating the catalyst components and the high-boiling aldehyde, i.e., a hydroformylation product of dicyclopentadiene is described in EP0374615, U.S. Pat. Nos. 5,817,884 and 5,773,667. The proposed methods are two-stage membrane separation by aromatic polyamide membrane using a rhodium complex compound containing a quaternary ammonium salt of high-molecular sulfonated-triphosphine as ligands.

U.S. Pat. Nos. 4,144,191 and 4,262,147 immobilize rhodium catalysts by the bonds with amine groups of polymer.

One pot sequential production of tricyclodecane dimethanol by hydroformylation of dicyclopentadiene followed by hydrogenation of the resultant dialdehyde is also known.

For example, British Patent No. 1170226 obtains tricyclodecane dimethanol by hydrogenation of hydroformylation product by increasing temperature and pressure after the hydroformylation.

Japanese Patent Application Laid-Open No. 55-118429 obtains tricyclodecane dimethanol by extraction with water and a polar solvent after hydroformylation and hydrogenation in a hydrocarbon solvent in the presence of a cobalt-phosphine catalyst.

Japanese Patent Application Laid-Open No. 63-119429 describes the reuse of the solution containing the catalyst separated from the tricyclodecane dimethanol layer after the hydroformylation and hydrogenation in a hydrocarbon solvent.

U.S. Pat. No. 2,880,241 produces tricyclodecane dimethanol by hydrogenating tricyclodecane dicarbaldehyde obtained by hydroformylation in an alcohol solvent. In the proposed method, the dialdehyde obtained by hydroformylation of dicyclopentadiene is converted into a acetal derivative stable at high temperatures to prevent the side reaction of the dialdehyde.

Japanese Patent Application Laid-Open No. 11-100339 directly produces tricyclodecane dimethanol by hydroformylation and sequential hydrogenation. The hydroformylation is conducted in a lower alcohol solvent in the presence of a tertiary amine and a rhodium catlyst of extremely reduced concentration using phosphite ligand.

The above methods of producing and recovering tricydodecane dicarbaldehyde and methods of producing tricyclodecane dimethanol by sequential hydrogenation of tricyclodecane dicarbaldehyde involve the following problems and are not necessarily satisfactory for industrial use.

The method of British Patent No. 750144 has problems of low yields of dialdehydes as low as about 28% as described in the working examples.

In the working examples of British Patent No. 1170226, although the yields are improved to about 80%, high reaction temperatures of 240° C. at highest and high reaction pressures of 25 MPa at highest are required, thereby making the process disadvantageous in apparatus costs, running costs and catalyst costs.

In the method of EP-A-186075 allowing a specific phosphine to be present in the reaction system to recover expensive rhodium compounds, the main product is tricyclodecene aldehyde resulting from hydroformylation of only one double bond of dicyclopentadiene and the yield of tricyclodecane dicarbaldehyde in the reaction product liquid is only 2.8%. Therefore, the proposed method cannot be suitable as a method of producing tricyclodecane dicarbaldehyde.

WO93/02024 describes the extraction of high-boiling aldehydes produced by rhodium-catalyzed hydroformylation of olefins with an extraction solvent comprising a primary alkanol and water. The inventors repeated the proposed process to find that the partition coefficient of dialdehydes into the extraction solvent was low, and as a result thereof, the efficiency of separation was poor, although the yields of tricyclodecane dicarbaldehyde is taught to be improved to about 45% in the working examples. To increase the recovery of rhodium, the addition of a large amount of sodium carboxylate was required. The sodium carboxylate deposited as solid matters during the recovery of dialdehydes from the reaction mixture, thereby complicating the system. The dialdehydes underwent aldol condensation due to heat history under the influence of the sodium carboxylate, thereby reducing the yields of dialdehydes significantly. In addition, the recovery of the organophosphorus compound was also not satisfactory. Further, since the extraction solvent was a primary alkanol such as methanol, the extracted dialdehyde changed to acetal to reduce the yield. Thus, the proposed process was not suitable for practical use.

Although U.S. Pat. No. 5,260,490 recovers 97 to 98% of rhodium by an aqueous solution of a specific organic phosphine in the working examples, the method requires a reaction pressure as high as 27 MPa and the use of expensive specific phosphine to recover rhodium. Another problem is that the aqueous solution of organic phosphine containing recovered rhodium as such cannot be directly reused in the next production of tricyclodecane dicarbaldehyde from dicyclopentadiene.

As mentioned above, the known methods involve problems such as low yields of dialdehydes, high catalyst costs due to the use of expensive rhodium in high concentration, poor separation efficiency between catalyst and produced dialdehydes, failure in separating the catalyst in reusable conditions, need for expensive reaction apparatus due to high reaction pressure of 25 MPa or higher, etc. Thus, any of the known methods are not satisfactory for industrial use.

In the methods of Japanese Patent Application Laid-Open Nos. 11-80067 and 11-80068, dicyclopentadiene is hydroformylated in the presence of a rhodium catalyst of extremely reduced concentration using a phosphite ligand while controlling a conjugated diene concentration. The inventors' study on the proposed method proved that the hydroformylation did not proceed sufficiently under the rhodium catalyst concentration taught therein. It was confirmed that the rhodium catalyst concentration should be increased to proceed the reaction with a sufficient reaction rate even when the concentration of conjugated diene was controlled to 150 ppm or lower or dienophile was coexisted as proposed in the documents. In addition, as described in Japanese Patent Application Laid-Open No. 61-501268, the use of phosphite ligands resulted in the production of high-boiling side products by the reaction of phosphite and dealdehyde during the separation of tricyclodecane dicarbaldehyde by distillation, etc. which was subject to heat history, thereby reducing the yields of dialdehyde. Further, tricyclodecane dicarbaldehyde was not obtained in high purity because the high-boiling products were decomposed during distillation to substances having a boiling point close to that of tricyclodecane dicarbaldehyde.

The methods proposed in EP 0374615, U.S. Pat. Nos. 5,817,884 and 5,773,667 are not of industrial use due to the use of expensive ligands and the insufficient durability of membrane. In addition, the proposed catalyst system needs a reaction pressure as high as 27 MPa to obtain high hydroformylation yields.

In the methods of U.S. Pat. Nos. 4,144,191 and 4,262,147, the dissolution of rhodium on the resin support into the reaction system cannot be avoided.

In the methods proposed by Japanese Patent Application Laid-Open Nos. 55-118429 and 63-119429 for producing tricyclodecane dimethanol in a hydrocarbon solvent, a layer containing only tricyclodecane dimethanol or a layer containing tricyclodecane dimethanol and a slight amount of hydrocarbon solvent can be obtained. However, since the target tricyclodecane dimethanol is extremely viscous, the operations for recovery, extraction and purification are difficult, thereby reducing the isolation yield of tricyclodecane dimethanol.

The process of producing tricyclodecane dimethanol in alcohol solvent proposed in U.S. Pat. No. 2,880,241 involves the following problems. Although the acetal derived from dialdehyde in the presence of alcohol solvent is stable at high temperatures, the hydrogenation of the acetal proceeds very slowly, thereby extremely reducing the productivity of the process of producing tricyclodecane dimethanol from tricyclodecane dicarbaldehyde. In addition, tricyclodecane dimethanol is difficult to separate by distillation from the acetal remaining not hydrogenated due to their close boiling points.

In the process of Japanese Patent Application Laid-Open No. 11-100339, the hydroformylation is conducted in a lower alcohol solvent in the presence of a tertiary amine compound and a rhodium-phosphite catalyst, and the product solution as such is hydrogenated in the presence of hydrogenation catalyst into tricyclodecane dimethanol. However, the hydroformylation does not proceed satisfactorily in the proposed rhodium catalyst concentration. When the hydroformylation is conducted in a rhodium catalyst concentration sufficiently high for promoting the reaction, rhodium constituting the complex of hydroformylation catalyst is reduced to metal state to deposit on the hydrogenation catalyst and the reaction apparatus, thereby making the recovery of the catalyst impossible. In addition, the activity of hydrogenation catalyst is extremely reduced in the product solution containing phosphite because phosphorus acts as catalyst poison. This requires a prolonged reaction time and severe conditions such as high temperature and high pressure. When the reaction temperature is raised, the reaction between the phosphite and aldehyde is promoted to form high-boiling by-product, thereby significantly reducing the yield of tricyclodecane dimethanol.

SUMMARY OF THE INVENTION

Accordingly, a first object of the present invention is to provide a method of producing tricyclodecane dicarbaldehyde and/or pentacyclopentadecane dicarbaldehyde by the hydroformylation of dicyclopentadiene and/or tricyclopentadiene, in high yields with low catalyst costs while enabling the use of inexpensive reaction apparatus due to relatively low reaction pressure.

A second object of the present invention is to provide a method of separating aldehyde without needing high temperatures as required in distillation. The separation method should enable the catalyst components to be efficiently separated from various aldehydes and reused in the next hydroformylation. Further, the separation method should provide high-boiling aldehyde in conditions suitable for converting them into alcohols, carboxylic acids, amine derivatives, etc.

A third object of the present invention is to provide an industrially advantageous method of producing tricyclodecane dimethanol and/or pentacyclopentadecane dimethanol by hydroformylating dicyclopentadiene and/or tricyclopentadiene to tricyclodecane dicarbaldehyde and/or pentacyclopentadecane dicarbaldehyde and sequentially hydrogenating the dialdehydes, in high yields with low catalyst costs while enabling the use of inexpensive reaction apparatus due to relatively low reaction pressure.

As a result of extensive study with the view of solving the above problems, the inventors have found that in a method of producing tricyclodecane dicarbaldehyde and/or pentacyclopentadecane dicarbaldehyde by hydroformylating dicyclopentadiene and/or tricyclopentadiene with hydrogen and carbon monoxide in a hydroformylation solvent in the presence of a catalyst comprising a rhodium compound and an organophosphorus compound, the catalyst components and dialdehydes (tricyclodecane dicarbaldehyde and/or pentacyclopentadecane dicarbaldehyde) are easily and effectively separated by contacting a reaction product liquid containing the dialdehydes with a polyhydric alcohol having 2 to 6 carbon atoms, thereby extracting the dialdehydes into the polyhydric alcohol while retaining the catalyst components in the hydroformylation solvent layer.

The inventors have further found that the transfer of a rhodium compound into the extraction solvent is effectively prevented by conducting the extraction process in an atmosphere having an oxygen concentration of 1000 ppm or less, and that the dissolution of an organophosphorus compound into the extraction solvent can be reduced to substantially negligible level by using an organic phosphorus compound having a solubility to hydrocarbon solvent (hydroformylation solvent) ten times higher than to the extraction solvent.

In addition, the inventors have found that corresponding tricyclodecane dimethanol and/or pentacyclopentadecane dimethanol are produced in high yield and with low costs by a subsequent catalytic hydrogenation of the tricyclodecane dicarbaldehyde and/or pentacyclopentadecane dicarbaldehyde thus obtained.

The present invention has been accomplished by these findings.

Accordingly, a first aspect of the present invention is a method of producing tricyclodecane dicarbaldehyde and/or pentacyclopentadecane dicarbaldehyde, comprising (1) a first step of hydroformylating dicyclopentadiene and/or tricyclopentadiene with hydrogen and carbon monoxide in a hydroformylation solvent comprising a hydrocarbon compound in the presence of a catalyst comprising a rhodium compound and an organophosphorus compound, thereby obtaining a hydroformylation product liquid containing tricyclodecane dicarbaldehyde and/or pentacyclopentadecane dicarbaldehyde; and (2) a second step of mixing an extraction solvent comprising a polyhydric alcohol having 2 to 6 carbon atoms with the hydroformylation product liquid, and allowing the resultant mixture to separate into a hydrocarbon compound layer and an extraction solvent layer, thereby transferring the tricyclodecane dicarbaldehyde and/or pentacyclopentadecane dicarbaldehyde into the extraction solvent layer while retaining the catalyst components in the hydrocarbon compound layer.

A second aspect of the present invention is a method in which the extraction process of the second step mentioned above is conducted in an atmosphere having an oxygen concentration of 1000 ppm or lower.

A third aspect of the present invention is a method of producing tricyclodecane dimethanol and/or pentacyclopentadecane dimethanol, comprising (1) a first step of hydroformylating dicyclopentadiene and/or tricyclopentadiene with hydrogen and carbon monoxide in a hydroformylation solvent comprising a hydrocarbon compound in the presence of a catalyst comprising a rhodium compound and an organophosphorus compound, thereby obtaining a hydroformylation product liquid containing tricyclodecane dicarbaldehyde and/or pentacyclopentadecane dicarbaldehyde; (2) a second step of mixing an extraction solvent comprising a polyhydric alcohol having 2 to 6 carbon atoms with the hydroformylation product liquid, and allowing the resultant mixture to separate into a hydrocarbon compound layer and an extraction solvent layer, thereby transferring the tricyclodecane dicarbaldehyde and/or pentacyclopentadecane dicarbaldehyde into the extraction solvent layer while retaining the catalyst components in the hydrocarbon compound layer; and (3) a third step of subjecting the extraction solvent layer obtained in the second step to catalytic hydrogenation, thereby converting the tricyclodecane dicarbaldehyde and/or pentacyclopentadecane dicarbaldehyde into corresponding tricyclodecane dimethanol and/or pentacyclopentadecane dimethanol.

DETAILED DESCRIPTION OF THE INVENTION

The hydroformylation of dicyclopentadiene and sequential hydrogenation to tricyclodecane dimethanol is shown in the reaction scheme (I), and the hydroformylation of tricyclopentadiene and sequential hydrogenation to pentacyclopentadecane dimethanol is shown in the reaction scheme (II).

complex may be prepared in advance and added to a reaction vessel. In a preferred embodiment of the present invention, Rh(acac)(CO) as a catalyst precursor is reacted with an organophosphorus compound in the presence of a solvent, and then the resultant product is introduced into a reaction vessel together with an excess of free organophosphorus compound, thereby forming catalytically active rhodium-organophosphorus complex. It is sufficient for achieving the object of the present invention that the active rhodium-organophosphorus catalyst is present in the reaction system during the hydroformylation in the presence of hydrogen and carbon monoxide.

The organophosphorus compound, which forms hydroformylation catalyst together with the rhodium compound, may be phosphite or phosphine. It has been known that a phosphite is effective for hydroformylation of internal olefins such as dicyclopentadiene and tricyclopentadiene (U.S. Pat. Nos. 3,499,933 and 4,443,638). It is preferred in the present invention to use known phosphites which are represented by the formula: $P(-OR^1)(-OR^2)(-OR^3)$ wherein $R^1$, $R^2$ and $R^3$ are each aryl or alkyl which may be substituted, and have an electronic parameter ($\nu$) of 2080 to 2090 cm$^{-1}$ and a steric parameter ($\theta$) of 135 to 190 degrees. The electronic parameter ($\nu$) and the steric parameter ($\theta$) are defined in C. A. Tolman, Chemical Reviews, vol. 77, p 313, 1977. The electronic parameter ($\nu$) is used to rank electronic

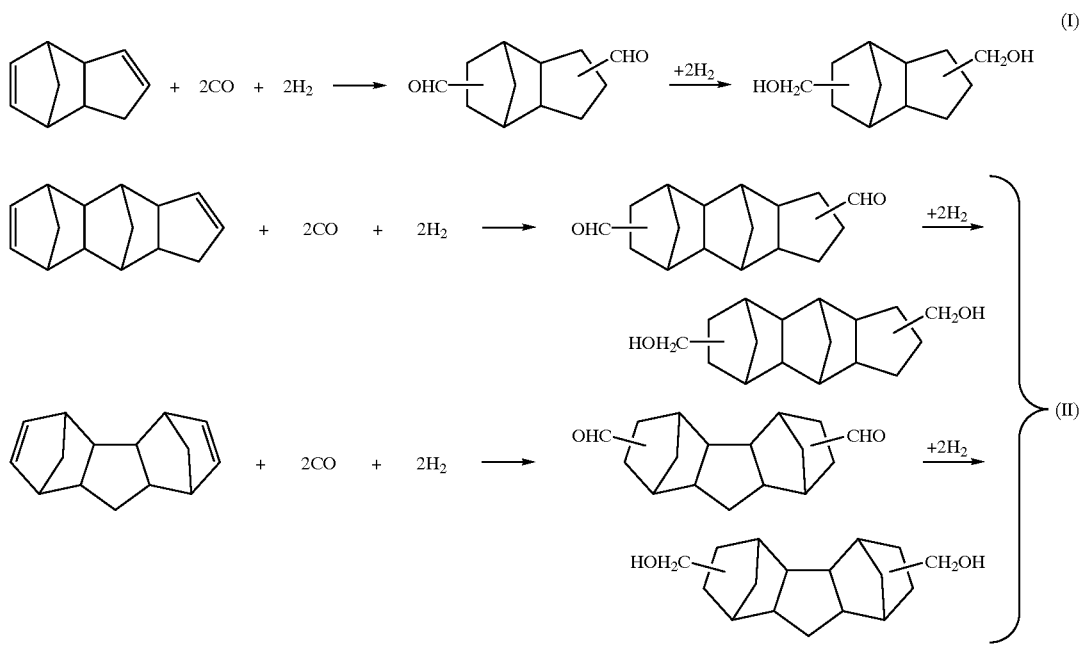

(I) Hydroformylation

The rhodium compound used in the first step of the present invention as a precursor for the hydroformylation catalyst is not strictly limited in its form as far as it forms a complex with an organophosphorus compound and shows activity of hydroformylation in the presence of hydrogen and carbon monoxide. Examples of such rhodium compound include Rh(acac)(CO)$_2$, Rh$_2$O$_3$, Rh$_4$(CO)$_{12}$, Rh$_6$(CO)$_{16}$ and Rh(NO$_3$)$_3$. The catalyst precursor may be added to a starting mixture together with an organophosphorus compound to create a catalytically active rhodium hydride-carbonyl-phosphorus complex in a reaction vessel. Alternatively, the rhodium hydride-carbonyl-phosphorus effect of phosphorus compounds in the formation of metal complex and is calculated based on the carbonyl stretching frequencies of Ni-carbonyl complex. The steric parameter ($\theta$) is used to evaluate the steric effect of phosphorus compounds and is calculated from cone angles of molecular models. Examples of $R^1$, $R^2$ and $R^3$ are aryl such as phenyl and naphthyl which may be substituted by methyl, ethyl, isopropyl, n-butyl, t-butyl or methoxy; aliphatic alkyl such as methyl, ethyl, isopropyl, n-butyl and t-butyl; and alicyclic alkyl such as cyclopentyl and cyclohexyl which may be substituted by lower alkyl such as methyl, ethyl, isopropyl, n-butyl and t-butyl. Preferred phosphites include triphenylphosphite, tris(2-t-buthylphenyl)phosphite, tris(3- methyl-6-t-butylphenyl)phosphite, tris(3-methoxy-6-t-butylphenyl)phosphite, tris(2,4-di-t-butylphenyl)phosphite and di(2-t-butylphenyl)-t-butylphosphite, although not restricted thereto. These phosphites may be used alone or in combination of two or more. In addition to the above triorganophosphites, also usable are bisphosphites described in Japanese Patent Application Laid-Open Nos. 61-501268, 8-165266, 8-337550, 10-45776 and 10-130190. Further, phosphite ligands having asymmetric carbon may be used.

Phosphines, particularly hindered alkylphosphines are known to be effective for hydroformylating internal olefins such as dicyclopentadiene and tricyclopentadiene (U.S. Pat. Nos. 3,168,553, 3,239,566 and 3,511,880). Preferred is a tertiary phosphine substituted by alkyl, arylalkyl, cycloalkyl such as cyclohexyl and aryl such as phenyl which may be substituted by one or more alkyl. Specific examples of the tertiary phosphine includes trialkylphosphines such as tri-n-butylphosphine, tricyclohexylphosphine and dicycohexyl-n-octylphosphine; triarylphosphines such as triphenylphosphine, tri-o-tolkylphosphine and trinaphthylphosphine; arylalkylphosphines such as dicyclohexylphenylphosphine, cyclohexyldiphenylphosphine and diphenyl-n-hexylphosphine. Also usable are bidentate chelate phosphine such as α,α'-bis(diphenylphosphino)-o-xylene, 2,2'-bis(diphenylphosphinomethyl)-1,1'-biphenyl, trans-1,2-bis(diphenylphosphinomethyl)cyclobutene, 1,4-bis(diphenylphosphino)butane and 1,2-bis(diphenylphosphino)ethane; and 2,2'-bis(diphenylphosphino)-1,1'-binaphthyl (BINAP) and its derivatives widely used as asymmetric ligands. Of the above phosphines, tricycloalkylphosphines having a steric parameter ($\theta$) of 135 to 190° are preferably used in the present invention. Specific examples thereof include tricyclopropylphosphine, tricyclobutylphosphine, tricyclopentylphosphine, tricyclohexylphosphine, tricycloheptylphosphine and tricylooctylphosphine, although not restricted thereto. These phosphines may be used alone or in combination of two or more.

The organophosphorus compound is used in an amount of 1 to 400 times, preferably 3 to 200 times the molar amount of rhodium metal in a hydroformylation solution. With the use of the organophosphorus compound within such a range, dialdehydes are obtained in satisfactory hydroformylation rates.

The hydroformylation in the present invention may be carried out in the absence of a solvent, but preferably in the presence of an organic solvent inert to the reaction. After the completion of hydroformylation, the reaction product liquid containing dialdehyde is brought into contact with an extraction solvent comprising a polyhydric alcohol having 2 to 6 carbon atoms and phase-separated, thereby extracting the dialdehyde into the extraction solvent while retaining the catalyst component in the hydroformylation solvent layer. To ensure the phase separation, it is preferred that the hydroformylation solvent is easy to separate from the polyhydric alcohol. Examples of such hydroformylation solvent are aromatic hydrocarbons, aliphatic hydrocarbons and alicyclic hydrocarbons.

The aromatic hydrocarbons may include benzene, methylbenzenes such as toluene, xylene, mesitylene and pseudocumene, ethylbenzenes such as ethylbenzene, diethylbenzene and triethylbenzene, propylbenzenes such as isopropylbenzene, 1,3-diisopropylbenzene and 1,4-diisopropylbenzene, and other alkylbenzenes. The aliphatic hydrocarbons may include pentane, hexane, heptane, octane, isooctane, dodecane and decane, and not limited thereto as far as they are liquid under normal temperature and pressure.

The alicyclic hydrocarbons are preferably cyclohexane, cyclooctane, cyclododecane, decalin and methylcyclohexane. Solvents having a polar functional group such as ketones and esters, and solvents having an atom other than carbon and hydrogen are not preferable as the hydroformylation solvent due to their low partitioning ability and their adverse affect on the catalyst systems.

The amount of rhodium compound is preferably 1 to 5000 ppm, more preferably 5 to 2000 ppm and particularly preferably 50 to 2000 ppm in terms of rhodium metal based on the starting dicyclopentadiene and/or tricyclopentadiene. When the amount is 10 ppm or more, it is preferred to recover and reuse the rhodium catalyst.

The hydroformylation is carried out at 40 to 160° C., preferably 70 to 140° C. and particularly preferably 80 to 140° C. under a pressure of 1.0 to 15 MPa. When the reaction temperature is lower than 40° C., the hydroformylation proceeds slowly. When higher than 160° C., side reactions associated with dicyclopentadiene, tricyclopentadiene and hydroformylation products become significant, thereby reducing the reaction yield. When the pressure is lower than 1.0 MPa, the hydroformylation proceed slowly. A pressure higher than 15 MPa requires a high-pressure apparatus to increase apparatus costs. Molar ratio of hydrogen and carbon monoxide in hydrogen/carbon monoxide mixed gas being introduced into the hydroformylation system is selected from the range of 0.2 to 5.0. A molar ratio outside the above range deactivates the hydroformylation and reduce the selectivity to dialdehyde.

The starting dicyclopentadiene is preferred to be highly pure. The presence of impurities such as butadiene, isoprene, cyclopentadiene and 1,3-pentadiene should be minimized, if possible. However, even if a highly pure dicyclopentadiene is used, it is practically impossible to avoid the presence of cyclopentadiene because it is inevitably formed by depolymerization of dicyclopentadiene under hydroformylation conditions. Therefore, the hydroformylation should be conducted under such conditions as to proceed the hydroformylation irrespective of the presence of a small amount of cyclopentadiene.

The starting tricyclopentadiene is easily produced from dicyclopentadiene. Dicyclopentadiene is subjected to both depolymerization and polymerization on heating to form tricyclopentadiene and tetra- and pentacyclopentadiene. Tricyclopentadiene is easily separated from a mixture of cyclopentadiene monomer and oligomers by distillation. As shown in the reaction formula (II), tricyclopentadiene includes two isomers.

In the present invention, the hydroformylation is carried out in continuous feeding manner in which the hydroformylation is continued while continuously feeding the starting dicyclopentadiene and/or tricyclopentadiene directly or as a solution into a reactor containing a rhodium-organophosphorus catalyst, solvent and a mixed gas of hydrogen and carbon monoxide. In this method, the thermal decomposition of dicyclopentadiene and/or tricyclopentadiene into cyclopentadiene which inhibits the hydroformylation can be minimized, thereby ensuring a high reaction rate and a good yield. It is preferred to dilute dicyclopentadiene and/or tricyclopentadiene with a solvent to maintain them flowable and feed them to a reactor at temperatures which do not cause the formation of cyclopentadiene by depolymerization.

(II) Extraction

The hydroformylation product is generally separated from the catalyst component, for example, by distillation, thin film evaporation and steam distillation. The hydroformylation products of the present invention, i.e., dialdehydes, cannot be separated from the reaction product liquid by a separation technique needing heat, such as distillation, due to their high boiling points and in view of the catalyst amount and the property of catalyst components. It is, of course, economically undesirable to dump the catalyst without reuse. Therefore, a separation method capable of separating the products from the catalyst components efficiently without heating is required.

In the method of the present invention, the reaction product liquid after completion of hydroformylation is brought into contact with an extraction solvent comprising a polyhydric alcohol having 2 to 6 carbon atoms without or after dilution by a hydrocarbon compound same as or different from that used as the hydroformylation solvent, thereby extracting only the produced dialdehydes into the extraction solvent while retaining the catalyst component in the hydroformylation solvent layer, followed by phase separation. Examples of the polyhydric alcohol include ethylene glycol, 1,3-propanediol, 1,2-propanediol, 1,4-butanediol, 1,2-butanediol, 1,3-butanediol, 2,3-butanediol, pentanediol isomers, neopentyl glycol, hexanediol, glycerol, pentaerythritol and trimethylolpropane. Of the above, ethylene glycol, propanediols and butanediols are preferably used due to their relatively low boiling points, low costs and easiness of handling. The polyhydric alcohols may be used alone or in combination of two or more. The polyhydric alcohol may contain water up to 50% by weight of the polyhydric alcohol, and the addition of water increases the partition coefficients of dialdehydes and catalyst components between two liquid phases.

To achieve a sufficient phase separation into two layers, the hydroformylation solvent and the extraction solvent are preferred to be different in their densities. A preferred combination of the hydroformylation solvent and the extraction solvent may be methylcyclohexane and ethylene glycol, although not restricted thereto and suitably selected depending on the property and kind of catalyst system and dialdehyde.

The partition of dialdehyde between the hydroformylation solvent and the extraction solvent is an equilibrium process. Also, the partition of the catalyst components, i.e., rhodium and the organophosphorus compound, between the solvents is an equilibrium process. The partition at equilibrium of the organophosphorus compound ligands depends on their kind, and the partition of rhodium changes accordingly. Therefore, it is preferred to use an organophosphorus compound having a high solubility to the hydroformylation solvent (hydrocarbon compound) and a low solubility to the extraction solvent. By the use of an organophosphorus compound having a solubility to the hydroformylation solvent 10 times higher than that to the extraction solvent, the partition coefficient of the organophosphorus compound to the hydroformylation solvent becomes 10 or larger, thereby sufficiently preventing the organophosphorus compound from transferring into the extraction solvent. By selecting an organophosphorus compound having a solubility to the hydroformylation solvent 100 times higher than that to the extraction solvent, the partition coefficient of the organophosphorus compound to the hydroformylation solvent reaches 100 or larger, thereby easily reducing the transfer of the organophosphorus compound into the extraction solvent to 1% or lower. For example, triphenylphosphine and tris (2,4-di-t-butylphenyl)phosphite are highly soluble in hydroformylation solvent such as methylcyclohexane, but insoluble in ethylene glycol as the extraction solvent. Therefore, these organophosphorus compounds does not transfer into the extraction solvent. A metal salt may be added to the extraction system to make the transfer of rhodium and organophosphorus compound as the catalyst components as little as possible, or a salting-out agent may be added to facilitate the phase separation, without causing any disadvantage.

The volume ratio of the extraction solvent to the hydroformylation product liquid varies depending on the solubility of dialdehyde to the extraction solvent and the amount of dialdehyde being extracted. For example, when dialdehyde is highly soluble to the extraction solvent and present in the hydroformylation product liquid in a low concentration, the use of the extraction solvent in a small volume ratio (extraction solvent/reaction product liquid) is sufficient for practical extraction of dialdehyde. Higher volume ratio is required with increasing concentration of dialdehyde. When the solubility of dialdehyde to the extraction solvent is relatively low, the volume ratio of the extraction solvent and the hydroformylation product liquid may vary 10 to 0.1. It is preferred to conduct the extraction by several portions of extraction solvent to obtain increased extraction amount of dialdehyde with a small amount of the extraction solvent.

The extraction temperature is not strictly limited. Since temperatures higher than the hydroformylation temperature produce no technical advantage, temperatures equal to or lower than the hydroformylation temperature are practical. The extraction may be conducted in the same reactor as used for hydroformylation, or in an extraction vessel after introducing the hydroformylation product liquid from the reactor into the extraction vessel.

When the extraction is conducted in the reactor of hydroformylation, the remaining reaction product liquid can be reused in next run of hydroformylation while retaining the catalyst components in the reaction product liquid. When the extraction is conducted in an extraction vessel, the hydrocarbon compound layer containing the catalyst is returned to the reactor for reuse. The process of the present invention may be conducted in either batch or continuous process.

In some cases, the hydroformylation products, dialdehydes, react with a polyhydric alcohol used as the extraction solvent to form high-boiling acetals. The formation of acetals reduces the yields of dialdehydes, and in addition, extremely reduces the reaction rate of hydrogenation for producing tricyclodecane dimethanol and pentacyclopentadecane dimethanol, thereby resulting in poor productivity. Further, since the boiling points of the acetals are so close to those of tricyclodecane dimethanol and pentacyclopentadecane dimethanol, they cannot be separated by distillation. The formation of acetals can be prevented by the addition of a tertiary amine to the polyhydric alcohol.

Examples of the tertiary amine include aliphatic tertiary amines such as trimethylamine, triethylamine, tri-n-butylamine, tri-n-octylamine, triethanolamine, N-methyldiethanolamine and N,N-dimethylethanolamine; aromatic tertiary amines such as N,N-dimethylaniline, N,N-diethylaniline and triphenylaniline; and heterocyclic tertiary amines such as pyridine and quinoline. Of the above, triethanolamine, N-methyldiethanolamine and N,N-dimethylethanolamine are preferably used in the separation of the catalyst components and dialdehyde by extraction due to their low solubility to the hydrocarbon compounds and high solubility to the polyhydric alcohols. Triethanolamine, N-methyldiethanolamine and N,N-dimethylethanolamine are particularly preferable in obtaining tricyclodecane dicarbaldehyde and pentacyclopentadecane dicarbaldehyde by distillation immediately after the extraction using ethylene glycol, propanediols and butanediols as the polyhydric alcohol because their boiling points are higher than those of the diols. These tertiary amine may be used alone or in combination of two or more. The addition amount thereof is not strictly limited as far as the formation of acetals is effectively avoided.

The tertiary amine may be added in the extraction process of the second step for separating the catalyst components and aldehyde from the hydroformylation product liquid, or at any stage after the extraction and just before the hydrogenation of the third step. When added in the extraction process of the second step, triethanolamine, N-methyldiethanolamine and N,N-dimethylethanolamine are preferably used due to their high compatibility with the polyhydric alcohol. When added between the extraction and the hydrogenation of the third step, preferably used are aliphatic tertiary amines such as trimethylamine, triethylamine, tri-n-butylamine, tri-n-octylamine, triethanolamine, N-methyldiethanolamine and N,N-dimethylethanolamine; aromatic tertiary amines such as N,N-dimethylaniline, N,N-diethylaniline and triphenylaniline; and heterocyclic tertiary amines such as pyridine and quinoline.

The extraction process of the present invention is preferably conducted in an atmosphere with an oxygen concentration of 1000 ppm or lower. In an extraction atmosphere with an oxygen concentration over 1000 ppm, the phosphines and the phosphites are oxidized to form oxides, thereby reducing the catalyst activity when reused. This phenomenon is known in the art. In addition, the inventors have found that the transfer of rhodium into the extraction solvent is largely affected by the coexistence of oxygen. Namely, when the extraction is carried out in the presence of oxygen, the transfer of rhodium into the extraction solvent becomes non-negligible to make the recycling of the catalyst impossible. The reason for this is presumed that the produced dialdehyde is oxidized to carboxylic acid which in turn forms a rhodium carboxylate easily transferring into the extraction solvent, in consideration of the fact that the transferring amount of the organophosphorus compound into the extraction solvent does not change during the extraction in the presence of oxygen. This phenomenon has been first recognized in the separation method by extraction of the present invention in which the hydroformylation product liquid is contacted with the extraction solvent comprising the polyhydric alcohol having 2 to 6 carbon atoms, and does not ever found in the known methods of separating the catalyst components and aldehydes by extraction. Thus, such a phenomenon has been first found by the inventors and hitherto unreported.

The transferring amount of rhodium into the extraction solvent is reduced by regulating the oxygen concentration in the extraction atmosphere to 1000 ppm or lower, preferably 100 ppm or lower. Atmosphere with an oxygen concentration of 1000 ppm or lower may be created practically by replacing the extraction atmosphere with carbon monoxide and hydrogen used in the hydroformylation or inert gas such as nitrogen, helium and argon. Since the polyhydric alcohol for use in extraction contains oxygen, the deaeration prior to its use to reduce the oxygen concentration is effective. The deaeration may be conducted by distillation under reduced pressure or blowing of nitrogen, carbon monoxide or hydrogen gas into the polyhydric alcohol, thereby reducing the dissolved oxygen concentration. It is preferred to subject the hydrocarbon compound to similar treatment.

From the polyhydric alcohol, the dialdehyde is isolated by known methods such as distillation. Alternatively, the produced dialdehyde may be converted to corresponding dimethanol with hydrogen in the presence of a hydrogenation catalyst without separating from the polyhydric alcohol after or without adding suitable solvent. The dialdehyde may be converted to a high-boiling amine by reductive amination using ammonia and hydrogen.

(III) Catalytic Hydrogenation

The catalyst used in the third step for hydrogenating tricyclodecane dicarbaldehyde and pentacyclopentadecane dicarbaldehyde may be known metal catalysts having ability of hydrogenation, for example, Group VIII metals of the Periodic Table such as nickel, cobalt, ruthenium, palladium, rhodium and platinum, copper chromite, copper-zinc, etc. These metal catalysts are used in element form, oxide form, supported form on inorganic carrier such as silica, alumina, diatomaceous earth and carbon, or metal complex form. Particularly preferred are Raney nickel, nickel/diatomaceous earth, copper chromite, ruthenium/carbon, ruthenium/alumina in view of high hydrogenation rate and easiness of recovery.

The hydrogenation may be conducted in batch manner where a catalyst slurry is charged into a stirring reactor and the catalyst is separated from the product solution after hydrogenation by sedimentation and filtration. Alternatively, a flowing liquid method may be employed, where a shaped catalyst is disposed in a tubular reactor and the product solution and hydrogen gas are permitted to flow over the catalyst. The amount of the catalyst to be used is not particularly limited and can be easily determined so as to produce tricyclodecane dimethanol and pentacyclopentadecane dimethanol in industrially advantageous productivity.

The hydrogenation temperature is 40 to 200° C., preferably 70 to 150° C., and the hydrogenation pressure is 10 MPa or lower. When lower than 40° C., the hydrogenation proceeds slowly, and temperatures higher than 200° C. cause side reactions of the target tricyclodecane dimethanol and pentacyclopentadecane dimethanol, thereby reducing the reaction efficiency. A reaction pressure higher than 10 MPa requires a high-pressure apparatus, thereby increasing apparatus costs.

The crude reaction solution containing tricyclodecane dimethanol, pentacyclopentadecane dimethanol and the polyhydric alcohol is easily recovered and purified by common methods. For example, tricyclodecane dimethanol and pentacyclopentadecane dimethanol are separated and purified by thin film evaporation or distillation of crude products after distilling off the solvent.

The present invention will be described in further detail by way of the following Examples which are not intended to limit the scope of the present invention thereto.

EXAMPLE 1

[Hydroformylation of Dicyclopentadiene]

Into a 500-ml magnetic stirring-type stainless autoclave equipped with a gas inlet and a sampling tube, were introduced 0.15 g (0.581 mmol) of $Rh(acac)(CO)_2$, 1.88 g (2.91 mmol) of tris-(2,4-di-t-butylphenyl)phosphite and 40 g of methylcyclohexane in a hydrogen/carbon monoxide (1/1 by mole) mixed gas atmosphere. Then, a liquid mixture of 250 g of dicyclopentadiene and 10 g of methylcyclohexane was continuously fed into the autoclave over two hours while maintaining the pressure at 7.0 MPa by introducing the hydrogen/carbon monoxide mixed gas. During the feeding of the liquid mixture, the temperature of the autoclave was kept at 130° C. After finishing the feeding of the liquid mixture, the contents in the autoclave were stirred at 130° C. for additional three hours to continue the reaction.

After the completion of the reaction, 414.3 g of reaction product liquid were taken out from the sampling tube at lower portion of the autoclave. The reaction product liquid consisted of two separated layers, lower one being rich in tricyclodecane dicarbaldehyde and upper one being rich in methylcyclohexane. The rhodium component and phosphorus components were present in both the layers.

After vigorously stirring the reaction product liquid to form a uniform suspension, a part thereof was analyzed by gas chromatography. The results showed that the conversion of dicyclopentadiene was 100% and the yield of tricyclodecane dicarbaldehyde was 97.6%. The yield of monoaldehyde produced by hydroformylation of one double bond of dicyclopentadiene was 2.4%.

EXAMPLE 2 TO 20

The hydroformylation of dicyclopentadiene and tricyclopentadiene were conducted in the same manner as in Example 1 while using phosphite or cyclohexylphosphine ligand and a hydroformylation solvent selected from methyclohexane, toluene, diisopropylbenzene, isooctane and cyclohexane. The results are shown in Table 1.

TABLE 1

| Example No. | Substrate | Ligand | Solvent | Feeding Time hr |
|---|---|---|---|---|
| 1 | DCPD | P(OPhB$_2$)$_3$ | methylcyclo-hexane | 2 |
| 2 | DCPD | PCy$_3$ | methylcyclo-hexane | 2 |
| 3 | TCPD | P(OPhB$_2$)$_3$ | methylcyclo-hexane | 2 |
| 4 | TCPD | PCy$_3$ | methylcyclo-hexane | 2 |
| 5 | DCPD | P(OPh)$_3$ | toluene | 2 |
| 6 | DCPD | PCy$_3$ | toluene | 2 |
| 7 | TCPD | P(OPh)$_3$ | toluene | 2 |
| 8 | TCPD | PCy$_3$ | toluene | 2 |
| 9 | DCPD | P(OPhB$_2$)$_3$ | diisopropyl-benzene | 2 |
| 10 | DCPD | PCy$_3$ | diisopropyl-benzene | 2 |
| 11 | TCPD | P(OPhB$_2$)$_3$ | diisopropyl-benzene | 2 |
| 12 | TCPD | PCy$_3$ | diisopropyl-benzene | 2 |
| 13 | DCPD | P(OPhB$_2$)$_3$ | isooctane | 2 |
| 14 | DCPD | PCy$_3$ | isooctane | 2 |
| 15 | TCPD | P(OPhB$_2$)$_3$ | isooctane | 2 |
| 16 | TCPD | PCy$_3$ | isooctane | 2 |
| 17 | DCPD | P(OPh)$_3$ | cyclohexane | 2 |
| 18 | DCPD | PCy$_3$ | cyclohexane | 2 |
| 19 | TCPD | P(OPh)$_3$ | cyclohexane | 2 |
| 20 | TCPD | PCy$_3$ | cyclohexane | 2 |

| Example No. | Reaction Time hr | Conversion of Substrate (%) | Yield of Dialdehyde (%) | Yield of Monoaldehyde (%) |
|---|---|---|---|---|
| 1 | 3 | 100 | 97.6 | 2.4 |
| 2 | 3 | 100 | 90.4 | 9.6 |
| 3 | 3 | 100 | 99.3 | 0.7 |
| 4 | 3 | 100 | 95.7 | 4.3 |
| 5 | 3 | 100 | 96.7 | 3.3 |
| 6 | 4 | 100 | 94.5 | 5.5 |
| 7 | 3 | 100 | 99.2 | 0.8 |
| 8 | 4 | 100 | 97.1 | 2.9 |
| 9 | 3 | 100 | 95.9 | 4.1 |
| 10 | 4 | 100 | 94.3 | 5.7 |
| 11 | 3 | 100 | 99.4 | 0.6 |
| 12 | 4 | 100 | 98.7 | 1.3 |
| 13 | 3 | 100 | 97.3 | 2.7 |
| 14 | 4 | 100 | 95.6 | 4.4 |
| 15 | 3 | 100 | 99.2 | 0.8 |
| 16 | 4 | 100 | 98.9 | 1.1 |
| 17 | 3 | 100 | 96.6 | 3.4 |
| 18 | 4 | 100 | 97.2 | 2.8 |
| 19 | 3 | 100 | 97.5 | 2.5 |
| 20 | 4 | 100 | 98.3 | 1.7 |

Note:
DCPD = Dicyclopentadiene
TCPD = Tricyclopentadiene
P(OPhB$_2$)$_3$ = Tris-(2,4-di-t-butylphenyl)phosphite
PCy$_3$ = Tricyclohexylphosphine
P(OPh)$_3$ = Triphenylphosphite

EXAMPLE 21

[Extraction]

Extraction was conducted in an atmosphere having an oxygen concentration of 100 ppm using an upright 1000-ml three-necked flask equipped with a glass rod for magnetic stirring, a thermometer for measuring liquid temperature, a vacuum cock for replacing the inner atmosphere of the flask with nitrogen or hydrogen/carbon monoxide, a cock at a lower portion for taking out the extract after extraction procedure, and a jacket for controlling the extraction temperature.

After vigorously stirring the reaction product liquid of Example 1, 100 g of the uniformly suspended reaction product liquid were charged in the flask. The reaction product liquid contained 85.66 g of tricyclodecane dicarbaldehyde, 1.78 g of monoaldehyde, 0.140 mmol of rhodium in terms of atom and 0.701 mmol of phosphorus in terms of atom.

After adding 300 g of methylcyclohexane used as the hydroformylation solvent and 300 g of ethylene glycol to the reaction product liquid, the resultant mixture was stirred at 25° C. for 30 minutes. After reaching the equilibrium, the stirring was stopped and the mixture was allowed to stand for 30 minutes to separate into two layers, upper layer containing the hydroformylation solvent and lower layer containing the extraction solvent.

The hydroformylation solvent layer (hydrocarbon compound layer) weighed 321.7 g and contained 8.57 g of tricyclodecane dicarbaldehyde, 0.53 g of monoaldehyde, 0.140 mmol of rhodium in terms of atom and 0.701 mmol of phosphorus in terms of atom.

The ethylene glycol layer (extraction solvent layer) weighed 378.3 g and contained 77.09 g of tricyclodecane dicarbaldehyde and 1.25 g of monoaldehyde. Substantially no transfer of rhodium and phosphorus into the ethylene glycol layer occurred because both the rhodium content and phosphorus content were below the detection limits of 0.003 mmol and 0.01 mmol each in terms of atom.

A small portion of tricyclodecane dicarbaldehyde and monoaldehyde extracted into the ethylene glycol layer were converted to acetals by the reaction with ethylene glycol, and the acetals were regarded as in tricyclodecane dicarbaldehyde and monoaldehyde, respectively, in the calculation of yields, partition coefficients, etc.

In the present invention, the extraction efficiency for compound X was evaluated by a partition coefficient (Kp) defined by:

Kp=(Concentration of X in extraction solvent)/(Concentration of X in hydroformylation solvent)

In the above extraction, Kp for tricyclodecane dicarbaldehyde was 7.65 and Kp for monoaldehyde was 2.01.

EXAMPLE 22

The hydroformylation solvent layer obtained in Example 21, which weighed 321.7 g and contained 8.57 g of tricyclodecane dicarbaldehyde, 0.53 g of monoaldehyde, 0.140 mmol of rhodium in terms of atom and 0.701 mmol of phosphorus in terms of atom, was re-extracted with 300 g of ethylene glycol in an atmosphere having an oxygen concentration of 100 ppm.

The resultant hydroformylation solvent layer (hydrocarbon compound layer) weighed 313.4 g and contained 0.06 g of tricyclodecane dicarbaldehyde, 0.21 g of monoaldehyde, 0.140 mmol of rhodium in terms of atom and 0.701 mmol of phosphorus in terms of atom.

The ethylene glycol layer (extraction solvent layer) weighed 308.3 g and contained 7.97 g of tricyclodecane dicarbaldehyde and 0.32 g of monoaldehyde. Substantially no transfer of rhodium and phosphorus into the ethylene glycol layer occurred because both the rhodium content and phosphorus content were below the detection limits of 0.003 mmol and 0.01 mmol each in terms of atom.

Kp for tricyclodecane dicarbaldehyde was 13.5 and Kp for monoaldehyde was 1.55.

EXAMPLE 23

Into a flask, were charged 100 g of the reaction product liquid obtained in Example 2. The reaction product liquid contained 80.34 g of tricyclodecane dicarbaldehyde, 7.20 g of monoaldehyde, 0.140 mmol of rhodium in terms of atom and 0.701 mmol of phosphorus in terms of atom.

After adding 300 g of methylcyclohexane used as the hydroformylation solvent, 300 g of ethylene glycol and 7.9 g of N-methyldiethanolamine to the reaction product liquid, the resultant mixture was stirred at 25° C. for three hours in an atmosphere having an oxygen concentration of 100 ppm. After reaching the equilibrium, the stirring was stopped and the mixture was allowed to stand for 30 minutes to separate into two layers, upper layer containing the hydroformylation solvent and lower layer containing the extraction solvent.

The hydroformylation solvent layer (hydrocarbon compound layer) weighed 322.7 g and contained 8.03 g of tricyclodecane dicarbaldehyde, 2.16 g of monoaldehyde, 0.140 mmol of rhodium in terms of atom and 0.701 mmol of phosphorus in terms of atom.

The ethylene glycol layer (extraction solvent layer) weighed 387.4 g and contained 72.31 g of tricyclodecane dicarbaldehyde and 5.04 g of monoaldehyde. Substantially no transfer of rhodium and phosphorus into the ethylene glycol layer occurred because both the rhodium content and phosphorus content were below the detection limits of 0.003 mmol and 0.01 mmol each in terms of atom.

The addition of N-methyldiethanolamine effectively prevented the acetal formation by the reaction of ethylene glycol with tricyclodecane dicarbaldehyde and monoaldehyde extracted into the ethylene glycol layer. The added N-methyldiethanolamine entirely transferred into the ethylene glycol layer.

Kp for tricyclodecane dicarbaldehyde was 7.50 and Kp for monoaldehyde was 1.96.

EXAMPLE 24 TO 40

The same extraction procedures as in Example 21 were repeated on the reaction product liquids containing different hydroformylation solvents, using ethylene glycol, propylene glycol, butanediol and polyhydric alcohols containing 25 volume % of water as the extraction solvents. The effect of tertiary amine in preventing the formation of acetal was examined by adding N-methyldiethanolamine and triethanolamine. The results are shown in Table 2.

Comparative Examples 1 to 6

Each hydroformylation product liquid obtained in Examples 1, 2, 4 and 10 was extracted with methanol or methanol/water (4/1 by volume) with or without adding sodium 2-ethylhexanoate. The results are shown in Table 2.

Methanol did not separate from the hydroformylation solvent to make the extraction impossible. When using methanol/water (4/1 by volume) as the extraction solvent, a large portion of rhodium and phosphorus transferred into the extraction solvent. The addition of sodium 2-ethylhexanoate was somewhat effective for preventing rhodium from transferring into the extraction solvent, but ineffective against phosphorus. The partition coefficient for dialdehyde was low and the acetal formation was found.

TABLE 2

|  | Hydroformylation liquid | Hydroformylation solvent | Extraction solvent | Additive amine |
|---|---|---|---|---|
| Examples | | | | |
| 21 | Example 1 | methylcyclohexane | ethylene glycol | — |
| 22 | Example 21 | methylcyclohexane | ethylene glycol | — |
| 23 | Example 2 | methylcyclohexane | ethylene glycol | (a) |
| 24 | Example 4 | methylcyclohexane | ethylene glycol | (b) |
| 25 | Example 2 | methylcyclohexane | 1,3-propanediol | (a) |
| 26 | Example 3 | methylcyclohexane | 1,4-butanediol | (b) |
| 27 | Example 1 | methylcyclohexane | glycerol | (b) |
| 28 | Example 5 | toluene | ethylene glycol/$H_2O$ | — |
| 29 | Example 6 | toluene | ethylene glycol/$H_2O$ | (b) |
| 30 | Example 8 | toluene | 1,3-propanediol | (a) |
| 31 | Example 9 | diisopropylbenzene | ethylene glycol | — |
| 32 | Example 10 | diisopropylbenzene | ethylene glycol | (b) |
| 33 | Example 11 | diisopropylbenzene | 1,3-propanediol | (a) |
| 34 | Example 12 | diisopropylbenzene | ethylene glycol | (b) |
| 35 | Example 13 | isooctane | ethylene glycol | — |
| 36 | Example 14 | isooctane | ethylene glycol | (b) |
| 37 | Example 16 | isooctane | ethylene glycol | (a) |
| 38 | Example 17 | cyclohexane | ethylene glycol | — |
| 39 | Example 19 | cyclohexane | ethylene glycol | (b) |
| 40 | Example 20 | cyclohexane | ethylene glycol | (a) |
| Comparative Examples | | | | |
| 1 | Example 1 | methylcyclohexane | methanol | — |
| 2 | Example 2 | methylcyclohexane | methanol | — |
| 3 | Example 2 | methylcyclohexane | methanol/$H_2O$ | — |
| 4 | Example 2 | methylcyclohexane | methanol/$H_2O$ | (c) |

TABLE 2-continued

| | | | | |
|---|---|---|---|---|
| 5 | Example 4 | methylcyclo-hexane | methanol/H$_2$O | (c) |
| 6 | Example 10 | diisopropyl-benzene | methanol/H$_2$O | (c) |

| | Extraction solvent layer | | Partition coefficient (Kp) | | |
|---|---|---|---|---|---|
| | Rh (mmol) | P (mmol) | dialdehyde | monoaldehyde | Acetal formation |
| Examples | | | | | |
| 21 | ≦0.003 | ≦0.01 | 7.65 | 2.01 | occurred |
| 22 | ≦0.003 | ≦0.01 | 13.5 | 1.55 | occurred |
| 23 | ≦0.003 | ≦0.01 | 7.50 | 1.96 | none |
| 24 | ≦0.003 | ≦0.01 | 10.2 | 1.73 | none |
| 25 | 0.003 | 0.01 | 7.30 | 1.87 | none |
| 26 | 0.004 | 0.02 | 5.98 | 1.66 | none |
| 27 | 0.004 | 0.03 | 4.37 | 2.11 | none |
| 28 | 0.003 | 0.01 | 6.35 | 1.73 | occurred |
| 29 | ≦0.003 | ≦0.01 | 7.14 | 1.96 | none |
| 30 | 0.003 | 0.01 | 6.12 | 2.33 | none |
| 31 | ≦0.003 | ≦0.01 | 8.31 | 1.62 | occurred |
| 32 | ≦0.003 | ≦0.01 | 8.52 | 1.77 | none |
| 33 | 0.003 | 0.01 | 8.43 | 1.88 | none |
| 34 | ≦0.003 | ≦0.01 | 8.61 | 1.82 | none |
| 35 | ≦0.003 | ≦0.01 | 7.83 | 1.90 | occurred |
| 36 | ≦0.003 | ≦0.01 | 8.06 | 2.12 | none |
| 37 | ≦0.003 | ≦0.01 | 9.08 | 2.22 | none |
| 38 | ≦0.003 | ≦0.01 | 7.25 | 1.84 | occurred |
| 39 | ≦0.003 | ≦0.01 | 6.89 | 2.50 | none |
| 40 | ≦0.003 | ≦0.01 | 6.94 | 2.31 | none |
| Comparative Examples | | | | | |
| 1 | no phase separation | | — | — | occurred |
| 2 | no phase separation | | — | — | occurred |
| 3 | 0.063 | 0.432 | 1.21 | 1.18 | occurred |
| 4 | 0.010 | 0.084 | 2.10 | 0.98 | occurred |
| 5 | 0.013 | 0.105 | 1.83 | 0.85 | occurred |
| 6 | 0.024 | 0.175 | 1.52 | 0.96 | occurred |

(a)N-Methyldiethanolamine.
(b)Triethanolamine.
(c)Sodium 2-ethylhexanoate.
In any of Examples and Comparative Examples, extraction process was conducted in an atmosphere having an oxygen concentration of 100 ppm or lower.

EXAMPLE 41

[Distillation]

The ethylene glycol layer (387.4 g) from the extraction process in Example 23 was subjected to simple distillation under reduced pressure of 2 mmHg.

Ethylene glycol was first distilled and then N-methyldiethanolamine was distilled at 107° C. Tricyclodecane dicarbaldehyde was collected as a distillate at 130° C. The recovery of tricyclodecane dicarbaldehyde by the distillation was 99.3%, and no acetal, high-boiling product and low-boiling product were detected in the distillate.

EXAMPLE 42

After adding 8.85 g of N-methyldiethanolamine as in Example 41, the ethylene glycol layer from the extraction process in Example 21 was subjected to simple distillation under reduced pressure of 2 mmHg.

The recovery of tricyclodecane dicarbaldehyde by the distillation was 99.1%. Although the ethylene glycol layer from the extraction process of Example 21 contained a slight amount of acetal, no additional acetal formation was detected during the distillation process. Further, other high-boiling product and low-boiling product were not detected.

EXAMPLE 43

The ethylene glycol layer containing 10.0 g of triethanolamine from the extraction process in Example 24 was subjected to simple distillation under reduced pressure of 2 mmHg in the same manner as in Example 41.

Ethylene glycol was first distilled and then triethanolamine was distilled. Thereafter, pentacyclopentadecane dicarbaldehyde was collected as a distillate at 210° C. The recovery of the dialdehyde by the distillation was 98.7%, and no acetal, high-boiling product and low-boiling product were detected in the distillate.

EXAMPLE 44

The 1,4-butanediol layer containing 10.0 g of triethanolamine from the extraction process of Example 26 was subjected to simple distillation under reduced pressure of 2 mmHg in the same manner as in Example 41.

The distillate of pentacyclopentadecane dicarbaldehyde was obtained in a recovery of 98.2%. No acetal, high-boiling product and low-boiling product were detected in the distillate.

Comparative Example 7

The reaction product liquid of Example 1 was directly subjected to simple distillation under reduced pressure of 2 mmHg without the extraction process. The recovery of the tricyclodecane dicarbaldehyde by the distillation was 84.7%. High-boiling by-products which might be attributable to the reaction of the dialdehyde and the phosphite ligand remained as still residue.

Comparative Example 8

The reaction product liquid of Example 2 was directly subjected to simple distillation under reduced pressure of 2 mmHg without the extraction process. The recovery of tricyclodecane dicarbaldehyde by the distillation was 90.2%. High-boiling by-products which might be attributable to the reaction of the dialdehyde and the phosphite ligand or the reaction between the dialdehydes remained as still residue. The still residue was reused in the next run of hydroformylation, but showed a catalytic activity as low as 1/5 of the original activity or lower.

Comparative Example 9

The reaction product liquid of Example 3 was directly subjected to simple distillation under reduced pressure of 2 mmHg without the extraction process. When pentacyclopentadecane dicarbaldehyde started to be distilled after the distillation of pentacyclopentadecene monoaldehyde was completed, water was generated in the distillation system to reduce the degree of vacuum. After the generation of water became slight, the distillation was continued by keeping the degree of vacuum at 2 mmHg. The recovery of pentacyclopentadecane dicarbaldehyde by the distillation was as low as about 20%, and the pentacyclopentadecane dicarbaldehyde distillate contained a large amount of low-boiling products derived from the decomposition and loss of one of aldehyde groups of pentacyclopentadecane dicarbaldehyde, thereby failing to obtain dialdehyde with high purity. In addition, the still residue contained a large amount of high-boiling products.

Comparative Example 10

The reaction product liquid of Example 4 was directly subjected to simple distillation under reduced pressure of 2 mmHg without the extraction process. The recovery of pentacyclopentadecane dicarbaldehyde by the distillation was 70.2%. High-boiling by-products which might be attributable to the reaction of the dialdehyde and the phosphite ligand or the reaction between the dialdehydes remained as still residue. The still residue was reused in the next run of hydroformylation, but showed no catalytic activity.

EXAMPLE 45
[Hydroformylation of Dicyclopentadiene]

Into a 500-ml stainless magnetic stirring-type autoclave equipped with a gas inlet and a sampling tube, were introduced 0.15 g (0.581 mmol) of $Rh(acac)(CO)_2$, 7.51 g (11.64 mmol) of tris-(2,4-di-t-butylphenyl)phosphite and 40 g of methylcyclohexane. The internal atmosphere was replaced twice with 0.5 MPa nitrogen gas and three times with 0.5 MPa hydrogen/carbon monoxide (1/1 by mole) mixed gas, thereby regulating the internal oxygen concentration to 100 ppm or lower. Then, a liquid mixture of 250 g of dicyclopentadiene and 10 g of methylcyclohexane was continuously fed into the autoclave over two hours while maintaining the pressure at 5.0 MPa by introducing the hydrogen/carbon monoxide mixed gas. During the feeding of the liquid mixture, the temperature of the autoclave was kept at 100° C. After finishing the feeding of the liquid mixture, the contents in the autoclave were stirred at 100° C. for additional three hours to continue the reaction.

After the completion of the reaction, a portion of reaction product liquid was taken out from the sampling tube disposed at lower portion of the autoclave.

The results of gas chromatographic analysis thereof showed that the conversion of dicyclopentadiene was 100% and the yield of tricyclodecane dicarbaldehyde was 98.4%. The yield of monoaldehyde by-produced by hydroformylation of only one double bond of dicyclopentadiene was 1.6%. The starting dicyclopentadiene and the methylcyclohexane solvent were distilled prior to the use in hydroformylation and stored in nitrogen atmosphere to reduce the dissolved oxygen concentration.

[Extraction Test]

The extraction test was conduced using an upright, 0.5 MPa pressure-resistant 3-liter stainless apparatus equipped with a gas inlet, a liquid inlet, a sampling tube disposed at lower portion, a pressure-resistant sight glass, a sheathed thermometer for measuring the liquid temperature, a jacket for changing the extraction temperature, and a magnetic stirring device. The 3-liter extraction apparatus was purged twice with 0.5 MPa nitrogen gas and three times with 0.5 MPa hydrogen/carbon monoxide (1/1 by mole) mixed gas, thereby regulating the internal oxygen concentration to 100 ppm or lower. In to the apparatus, were charged 1000 g of ethylene glycol stored in nitrogen atmosphere, 0.70 g of N-methyldiethanolamine and 950 g of methylcyclohexane, while maintaining the internal pressure at 0.3 MPa by feeding the hydrogen/carbon monoxide (1/1 by mole) mixed gas. The reaction product liquid from a lower portion of the hydroformylation vessel was pumped into the extraction apparatus through a pipe while keeping the internal pressure of the extraction apparatus at 0.3 MPa. The resultant mixture was vigorously stirred at 25° C. for three hours. After reaching the equilibrium, the stirring was stopped and the mixture was allowed to stand for 30 minutes to separate into two layers, upper layer containing the hydrocarbon solvent and lower layer containing the extraction solvent. The hydrocarbon compound layer weighed 1038.6 g and contained 28.3 g of tricyclodecane dicarbaldehyde, 2.62 g of monoaldehyde, 0.581 mmol of rhodium in terms of atom and 11.64 mmol of phosphorus in terms of atom. The ethylene glycol layer weighed 1332.3 g and contained 329.3 g of tricyclodecane dicarbaldehyde and 2.29 g of monoaldehyde. Substantially no transfer of rhodium and phosphorus into the ethylene glycol layer occurred because both the rhodium content and phosphorus content were below the detection limits of 0.003 mmol and 0.01 mmol each in terms of atom.

In the present invention, the partition rate of tricyclodecane dicarbaldehyde or monoaldehyde into the extraction solvent is defined as follows.

Partition rate of X=(weight of X in extraction solvent)/(total weight of X)

In the above test, the partition rate was 92.1% for tricyclodecane dicarbaldehyde and 46.6% for monoaldehyde.

Kp was 9.07 for tricyclodecane dicarbaldehyde and 0.68 for monoaldehyde. The solubility of tris-(2,4-di-t-butylphenyl)phosphite used as the organophosphorus ligand to methylcyclohexane (MCH) was 32.8 g/100 g MCH at 25° C., while the solubility to ethylene glycol was substantially zero because no dissolution was noticed at 25° C.

EXAMPLE 46
[Hydroformylation of Tricyclopentadiene]

Into a 500-ml stainless magnetic stirring-type autoclave equipped with a gas inlet and a sampling tube, were introduced 0.0334 g (0.129 mmol) of $Rh(acac)(CO)_2$, 2.50 g (3.86 mmol) of tris-(2,4-di-t-butylphenyl)phosphite and 40 g of methylcyclohexane. The internal atmosphere was replaced twice with 0.5 MPa nitrogen gas and three times with 0.5 MPa hydrogen/carbon monoxide (1/1 by mole) mixed gas, thereby regulating the internal oxygen concentration to 100 ppm or lower. Then, a liquid mixture of 250 g of tricyclopentadiene and 60 g of methylcyclohexane was continuously fed into the autoclave over two hours while maintaining the internal pressure at 5.0 MPa by introducing the hydrogen/carbon monoxide mixed gas. During the feeding of the liquid mixture, the internal temperature of the autoclave was kept at 100° C. After finishing the feeding of the liquid mixture, the contents in the autoclave were stirred at 100° C. for additional three hours to continue the reaction.

After the completion of the reaction, a portion of reaction product liquid was taken out from the sampling tube disposed at lower portion of the autoclave.

The results of gas chromatographic analysis thereof showed that the conversion of tricyclopentadiene was 100% and the yield of pentacyclopentadecane dicarbaldehyde was 99.0%. The yield of monoaldehyde by-produced by hydroformylation of only one double bond of tricyclopentadiene was 1.0%. The starting dicyclopentadiene and the methylcyclohexane solvent were distilled prior to the use in hydroformylation and stored in nitrogen atmosphere.

[Extraction Test]

The extraction test was conduced using an upright, 0.5 MPa pressure-resistant one-liter stainless apparatus equipped with a gas inlet, a liquid inlet, a sampling tube disposed at lower portion, a pressure-resistant sight glass, a sheathed thermometer for measuring the liquid temperature, a jacket for changing the extraction temperature, and a magnetic stirring device. The one-liter extraction apparatus was purged twice with 0.5 MPa nitrogen gas and three times with 0.5 MPa hydrogen/carbon monoxide (1/1 by mole) mixed gas, thereby regulating the internal oxygen concentration to 100 ppm or lower. In to the apparatus, were charged 365 g of ethylene glycol stored in nitrogen atmosphere after distillation and 0.16 g of N-methyldiethanolamine, while maintaining the internal pressure at 0.3 MPa by feeding the hydrogen/carbon monoxide (1/1 by mole) mixed gas. The reaction product liquid from a lower portion of the hydroformylation vessel was pumped into the extraction apparatus through a pipe while keeping the internal pressure of the extraction apparatus at 0.3 MPa. The resultant mixture was vigorously stirred at 25° C. for three hours. After reaching the equilibrium, the stirring was stopped and the mixture was allowed to stand for 30 minutes to separate into two layers, upper layer containing the hydrocarbon compound and lower layer containing the extraction solvent. The hydrocarbon compound layer weighed 109.6 g and contained 6.53 g of pentacyclopentadecane dicarbaldehyde, 0.55 g of monoaldehyde, 0.129 mmol of rhodium in terms of atom and 3.86 mmol of phosphorus in terms of atom. The ethylene glycol layer weighed 488.2 g and contained 122.4 g of pentacyclopentadecane dicarbaldehyde and 0.60 g of monoaldehyde. Substantially no extraction of rhodium and phosphorus into the ethylene glycol layer occurred because both the rhodium content and phosphorus content were below the detection limits of 0.003 mmol and 0.01 mmol each in terms of atom.

The partition rate to the extraction solvent was 94.9% for pentacyclopentadecane dicarbaldehyde and 52.2% for monoaldehyde. The partition coefficient, Kp, was 4.21 for pentacyclopentadecane dicarbaldehyde and 0.25 for monoaldehyde.

Example 47

From 109.6 g of the methylcyclohexane solution, obtained in the extraction process of Example 46, containing rhodium and the phosphite, 60 g of methylcyclohexane were distilled off by vacuum distillation at 70° C. under 280 mmHg. Using the residual solution containing rhodium and the phosphite, the hydroformylation process and the extraction process of Example 46 were repeated five times. The yield of pentacyclopentadecane dicarbaldehyde (referred to as "PPD-dA") in each of replicates is shown in Table 3.

TABLE 3

|  | Replicate | | | | |
| --- | --- | --- | --- | --- | --- |
|  | 1 (Example 46) | 2 | 3 | 4 | 5 |
| Yield of PPD-dA | 99.0% | 98.4% | 99.2% | 98.5% | 98.4% |

Substantially no extraction of rhodium and phosphorus into the ethylene glycol layer occurred in the extraction of each replicate because both the rhodium content and phosphorus content in the ethylene glycol layer were below the detection limits of 0.003 mmol and 0.01 mmol each in terms of atom.

The ethylene glycol layers containing pentacyclopentadecane dicarbaldehyde from each extraction process of replicates 1 to 5 were collected and vacuum-distilled to distill off the major parts of ethylene glycol and pentacyclopentadecane dicarbaldehyde. The condensed residue was analyzed to determine the total amount of the catalyst components transferred into the ethylene glycol layer in the replicates 1 to 5. The results showed 1.4% (0.28% in each replicate) for rhodium and 0.3% (0.06% in each replicate) for phosphorus, each based on the charged amounts.

Comparative Example 11

The extraction process of Example 46 was repeated in the presence of oxygen and the same replicate runs as in Example 47 were conducted. The oxygen concentration of the extraction atmosphere, the yield of pentacyclopentadecane dicarbaldehyde (PPD-dA) and the ratios of rhodium and phosphorus transferred into the extraction solvent to the charged amounts are shown in Table 4.

TABLE 4

|  | Replicate | | | | |
| --- | --- | --- | --- | --- | --- |
|  | 1 | 2 | 3 | 4 | 5 |
| Oxygen concentration (ppm) | 8000 | 8000 | 8000 | 7000 | 5000 |
| Yield of PPD-dA (%) | 98.3 | 97.0 | 96.6 | 88.1 | 48.8 |
| Transferred amount (%) | | | | | |
| Rh | 12.3 | 15.0 | 15.4 | 9.2 | 5.6 |
| P | <0.3 | <0.3 | <0.3 | <0.3 | <0.3 |

EXAMPLE 48

[Hydrogenation]

Into a 200-ml stainless autoclave equipped with a stirring device, were charged 100 g of the ethylene glycol layer containing tricyclodecane dicarbaldehyde and monoaldehyde obtained in Example 21, 0.5 g of N-methyldiethanolamine and 5 g of Raney nickel. After replacing the internal atmosphere with hydrogen gas, stirring was begun and the temperature and the hydrogen gas pressure were regulated to 120° C. and 0.9 MPa. The reaction was continued for three hours under the above conditions. After no further absorption of hydrogen gas was detected, the reaction product solution was taken out from the autoclave after cooling and pressure release.

The conversion of tricyclodecane dicarbaldehyde was 100%, and no additional formation of acetal occurred during the hydrogenation except for the dialdehyde acetal formed during the extraction. The yield of tricyclodecane dimethanol based on the dialdehyde was 99.6%. The amount of acetal was 0.4% based on tricyclodecane dimethanol.

EXAMPLE 49

[Hydrogenation]

Into a 200-ml stainless autoclave equipped with a stirring device, were charged 100 g of the ethylene glycol layer containing tricyclodecane dicarbaldehyde, monoaldehyde and N-methyldiethanolamine obtained in Example 23, and 5 g of 5-wt % Ru/C. After replacing the internal atmosphere with hydrogen gas, stirring was begun and the temperature and the hydrogen gas pressure were regulated to 120° C. and 0.9 MPa. The reaction was continued for three hours under the above conditions. After no further absorption of hydrogen gas was detected, the reaction product solution was taken out from the autoclave after cooling and pressure release.

The conversion of tricyclodecane dicarbaldehyde was 100%, and no acetal formation occurred during the extraction and hydrogenation. The yield of tricyclodecane dimethanol based on the dialdehyde was 99.7% or higher.

EXAMPLE 50

[Extraction]

The extraction of the hydroformylation product liquid obtained in Example 3 was conducted in the same manner as in Example 21 except for using 300 g of ethylene glycol and 1.0 g of triethanolamine.

Substantially no extraction of rhodium and phosphorus into the ethylene glycol layer occurred because both the rhodium content and phosphorus content were below the detection limits of 0.003 mmol and 0.01 mmol each in terms of atom.

The addition of triethanolamine effectively prevented the acetal formation by the reaction of ethylene glycol with pentacyclopentadecane dicarbaldehyde or monoaldehyde extracted into the ethylene glycol layer. The added triethanolamine entirely transferred into the ethylene glycol layer.

Kp for pentacyclopentadecane dicarbaldehyde was 9.57 and Kp for monoaldehyde was 1.72.

[Hydrogenation]

Into a 200-ml stainless autoclave equipped with a stirring device, were charged 100 g of the above ethylene glycol layer containing pentacyclopentadecane dicarbaldehyde, monoaldehyde and triethanolamine and 5 g of Cu—Cr catalyst. After replacing the internal atmosphere with hydrogen gas, stirring was begun and the temperature and the hydrogen gas pressure were regulated to 120° C. and 0.9 MPa. The reaction was continued for three hours under the above conditions. After no further absorption of hydrogen gas was detected, the reaction product solution was taken out from the autoclave after cooling and pressure release.

The conversion of pentacyclopentadecane dicarbaldehyde was 100%, and no acetal formation occurred during the extraction and hydrogenation. The yield of tricyclodecane dimethanol based on the dialdehyde was 99.7% or higher.

EXAMPLE 51

[Extraction]

The hydroformylation product liquid of Example 4 was extracted in the same manner as in Example 50.

Kp for pentacyclopentadecane dicarbaldehyde was 10.2 and Kp for monoaldehyde was 1.73.

[Hydrogenation]

In the same manner as in Example 48, the hydrogenation was conducted except for using 100 g of the above ethylene glycol layer containing pentacyclopentadecane dicarbaldehyde, monoaldehyde and triethanolamine and 5 g of Raney nickel.

The conversion of pentacyclopentadecane dicarbaldehyde was 100%, and no acetal formation occurred during the extraction and hydrogenation. The yield of pentacyclopentadecane dimethanol based on the dialdehyde was 99.7% or higher.

EXAMPLE 52

The ethylene glycol layer (100 g) from the extraction process of Example 48 was added with 0.5 g of triethylamine and subjected to hydrogenation in the same manner as in Example 48 using 5 g of Raney nickel.

The conversion of tricyclodecane dicarbaldehyde was 100%, and no additional formation of acetal occurred during the hydrogenation except for the dialdehyde acetal formed in the extraction. The yield of tricyclodecane dimethanol based on the dialdehyde was 99.6%. The amount of acetal was 0.4% based on tricyclodecane dimethanol.

EXAMPLE 53

The ethylene glycol layer (100 g) from the extraction process of Example 48 was added with 0.5 g of N,N-dimethylethanolamine and subjected to hydrogenation in the same manner as in Example 48 using 0.5 g of 5-wt % Ru/C as the catalyst.

The conversion of tricyclodecane dicarbaldehyde was 100%, and no additional formation of acetal occurred during the hydrogenation except for the dialdehyde acetal formed during the extraction. The yield of tricyclodecane dimethanol based on the dialdehyde was 99.6%. The amount of acetal was 0.4% based on tricyclodecane dimethanol.

EXAMPLE 54

The ethylene glycol layer (100 g) from the extraction process of Example 48 was subjected to hydrogenation in the same manner as in Example 48 using 5 g of Raney nickel without adding a tertiary amine.

Although the conversion of tricyclodecane dicarbaldehyde was 100%, the formation of acetal occurred during the hydrogenation in addition to the dialdehyde acetal formed during the extraction. The yield of tricyclodecane dimethanol based on the dialdehyde was 85.7%. The amount of acetal was 14.3% based on tricyclodecane dimethanol.

Comparative Example 12

The hydroformylation product liquid obtained in Example 48 was added with 300 g of isopropanol to form a uniform mixture, 120 g of which was subjected to hydrogenation in the same manner as in Example 48 using 5 g of Raney nickel.

Although hydrogen was absorbed rapidly at initial stage of the reaction, the absorption became slower after 30 minutes, thereby failing to absorb the theoretical amount of hydrogen. The analysis of the reaction product liquid showed that the conversion of tricyclodecane dicarbaldehyde was 56% and the amount of acetal was 13.8%. The analysis of the hydrogenation product liquid showed that the recovery was less than 5% for rhodium and about 70% for phosphorus.

Comparative Example 13

The hydroformylation product liquid obtained in Example 50 was added with 300 g of isopropanol to form a uniform mixture, 120 g of which was subjected to hydrogenation in the same manner as in Example 48 using 5 g of Raney nickel.

Although hydrogen was absorbed rapidly at initial stage of the reaction, the absorption became slower after 30 minutes, thereby failing to absorb the theoretical amount of hydrogen. The analysis of the reaction product liquid showed that the conversion of pentacyclopentadecane dicarbaldehyde was 51% and the amount of acetal was 12.5%.

The hydrogenation was further continued for additional three hours under more severe conditions of 160° C. and 3.0 MPa. Although the conversion of pentacyclopentadecane dicarbaldehyde was increased to 92%, the acetal was not hydrogenated. High-boiling substances attributable to the reaction between the phosphite and pentacyclopentadecane dicarbaldehyde was formed in large quantities. The analysis of the hydrogenation product liquid showed that the recovery was less than 2% for rhodium and about 10% for phosphorus.

What is claimed is:

1. A method of producing tricyclodecane dicarbaldehyde and/or pentacyclopentadecane dicarbaldehyde, comprising:

a first step of hydroformylating dicyclopentadiene and/or tricyclopentadiene with hydrogen and carbon monoxide in a hydroformylation solvent comprising a hydrocarbon compound in the presence of a catalyst comprising a rhodium compound and an organophosphorus compound, thereby obtaining a hydroformylation product liquid containing tricyclodecane dicarbaldehyde and/or pentacyclopentadecane dicarbaldehyde; and a second step of mixing the hydroformylation product liquid with an extraction solvent comprising a polyhydric alcohol having 2 to 6 carbon atoms and selected from the group consisting of ethylene glycol, 1,3- propanediol, 1,4-butanediol, 1,2-butanediol, 1,3-butanediol, 2,3-butanediol, pentanediol isomers, neopentyl glycol, hexanediol, glycerol, pentaerythritol and tetetramnethylolpropane, and allowing the resultant mixture to separate into a hydrocarbon compound layer and an extraction solvent layer, thereby transferring the tricyclodecane dicarbaldehyde and/or pentacyclopentadecane dicarbaldehyde into the extraction solvent layer while retaining the catalyst components in the hydrocarbon compound layer.

2. The method according to claim 1, wherein the hydroformylation product liquid is further mixed with a hydrocarbon compound in the second step.

3. The method according to claim 2, wherein the hydrocarbon compound used as the hydroformylation solvent and the hydrocarbon compound added in the second step are the same.

4. The method according to claim 1, wherein the extraction process of the second step is conducted in the presence of a tertiary amine which has a boiling point higher than that of the polyhydric alcohol, and after the separation into the hydroformylation solvent layer containing the catalyst components and the extraction solvent layer containing the tricyclodecane dicarbaldehyde and/or pentacyclopentadecane dicarbaldehyde, the extraction solvent layer is distilled to obtain the tricyclodecane dicarbaldehyde and/or pentacyclopentadecane dicarbaldehyde.

5. The method according to claim 1, wherein the extraction solvent further comprises water.

6. The method according to claim 1, wherein the mixing of the hydroformylation product liquid with the extraction solvent or the mixing of the hydroformylation product liquid with the hydrocarbon compound and the extraction solvent is conducted in an atmosphere having an oxygen concentration of 1000 ppm or lower.

7. The method according to claim 1, wherein the organophosphorus compound has a solubility to the hydrocarbon compound ten times higher than the solubility to the extraction solvent.

8. A method of producing tricyclodecane dimethanol and/or pentacyclopentadecane dimethanol, comprising:
   a first step of hydroformylating dicyclopentadiene and/or tricyclopentadiene with hydrogen and carbon monoxide in a hydroformylation solvent comprising a hydrocarbon compound in the presence of a catalyst comprising a rhodium compound and an organophosphorus compound, thereby obtaining a hydroformylation product liquid containing tricyclodecane dicarbaldehyde and/or pentacyclopentadecane dicarbaldehyde;
   a second step of mixing the hydroformylation product liquid with an extraction solvent comprising a polyhydric alcohol having 2 to 6 carbon atoms and selected from the group consisting of ethylene glycol, 1,3-propanediol, 1,4-butanediol, 1,2-butanediol, 1,3-butanediol, 2,3-butanediol, pentanediol isomers, neopentyl glycol, hexanediol, glycerol, pentaerythritol and tetetramnethylolpropane, and allowing the resultant mixture to separate into a hydrocarbon compound layer and an extraction solvent layer, thereby transferring the tricyclodecane dicarbaldehyde and/or pentacyclopentadecane dicarbaldehyde into the extraction solvent layer while retaining the catalyst components in the hydrocarbon compound layer; and
   a third step of subjecting the extraction solvent layer obtained in the second step to catalytic hydrogenation, thereby converting the tricyclodecane dicarbaldehyde and/or pentacyclopentadecane dicarbaldehyde into corresponding tricyclodecane dimethanol and/or pentacyclopentadecane dimethanol.

9. The method according to claim 8, wherein the hydroformylation product liquid is further mixed with a hydrocarbon compound in the second step.

10. The method according to claim 9, wherein the hydrocarbon compound used as the hydroformylation solvent and the hydrocarbon compound added in the second step are the same.

11. The method according to claim 8, wherein the extraction process of the second step is conducted in the presence of a tertiary amine which has a boiling point higher than that of the polyhydric alcohol, and after the separation into the hydroformylation solvent layer containing the catalyst components and the extraction solvent layer containing the tricyclodecane dicarbaldehyde and/or pentacyclopentadecane dicarbaldehyde, the extraction solvent layer is distilled to obtain the tricyclodecane dicarbaldehyde and/or pentacyclopentadecane dicarbaldehyde.

12. The method according to claim 8, wherein the extraction solvent further comprises water.

13. The method according to claim 8, wherein the mixing of the hydroformylation product liquid with the extraction solvent or the mixing of the hydroformylation product liquid with the hydrocarbon compound and the extraction solvent is conducted in an atmosphere having an oxygen concentration of 1000 ppm or lower.

14. The method according to claim 8, wherein the organophosphorus compound has a solubility to the hydrocarbon compound ten times higher than the solubility to the extraction solvent.

15. The method according to claim 5, wherein the extraction solvent includes water in an amount of up to 50% by weight of the polyhydric alcohol.

16. The method according to claim 1, wherein the hydroformylation solvent and the extraction solvent have different densities.

17. The method according to claim 1, wherein the organophosphorus compound has a higher solubility in the hydroformylation solvent than in the extraction solvent.

18. The method according to claim 1, wherein the hydroformylation solvent is methylcyclohexane, and the extraction solvent is ethylene glycol.

\* \* \* \* \*